United States Patent [19]

Quin et al.

[11] Patent Number: 5,334,741
[45] Date of Patent: Aug. 2, 1994

[54] PHOSPHORYLATION WITH MONOMERIC METAPHOSPHATES

[75] Inventors: Louis D. Quin, Amherst, Mass.; Stefan Jankowski, Lodz, Poland

[73] Assignee: Research Corporation Technologies, Inc., Tucson, Ariz.

[21] Appl. No.: 916,661

[22] Filed: Jul. 20, 1992

[51] Int. Cl.$^5$ ............................................. C07F 9/02
[52] U.S. Cl. .................... 558/110; 558/106; 558/107; 558/108; 558/109; 8/181; 8/194; 8/196
[58] Field of Search ......................... 8/181, 194, 196; 558/110, 106, 107, 108, 109

[56] References Cited

U.S. PATENT DOCUMENTS 4,123,319 10/1978 Bjorklund et al. .................... 8/181

FOREIGN PATENT DOCUMENTS 4120085 1/1992 Fed. Rep. of Germany.

OTHER PUBLICATIONS

W. S. Zielinski et al., "Phenyl N-phenylphosphoroamidochloridate: A New Phosphorylating Agent", Synthesis, pp. 185-187, Mar. 1976.
Ermolenko, et al., SU,A,610,892, Derwent Publications Ltd., London, GB, May 15, 1978, Abstract.
Louis D. Quin et al.; Metaphosphate and Metaphosphomic Anhydride Formation by Thermolysis of 5,6-Oxaphosphabicyclo[2.2.2]octenes: Electrophilic α-Substitution on a Pyrrole; pp. 3389-3390; J. Am. Chem. Soc. 1985, 107.
Louis D. Quin et al.; The Mechanism of Fragmentation of Alkyl α-(Oxyimino) Benzylphosphonates; Use of Silica Gel as a Novel Hydroxylic Trapping Reactant for an Intermediate Alkyl Metaphosphate; pp. 6281-6282; Tetrahedron Letters, vol. 31, No. 44, 1990.
Louis D. Quin et al.; Phosphorylation of the Surface of Silica Gel by Ethyl Metaphosphate; pp. 555-556; J. Chem. Soc., Chem. Commun., 1988.
Louis D. Quin; Reaction Products of Alkyl Metaphosphates with Silica; Novel HPLC Packing; Abstract of presentation at Northeastern Regional Meeting of Amer. Chem. Soc.; Jun. 1991; Amherst, Mass.
Louis D. Quin et al.; Generation of Ester and Amide Dereivatives of Metaphosphoric Acid by Photolysis of 2,3-Oxaphosphabicyclo [2,2,2]Oct-5-Ene Derivatrives; pp. 2627-2630; Tetrahedron Letters vol. 29, No. 22, 1988.
Louis D. Quin et al.; Direct Detection of Two Metaphosphoramidates in −75° The Solutions by $^{31}$P NMR Spectroscopy; pp. 6473-6476; Tetrahedron Letters, vol. 3, No. 45; 1990.
Louis D. Quin et al.; Chemistry of the 2,3-Oxaphosphabicyclo [2.2.2]octene Ring System: Extrusin of Metaphosphates; 1991; vol. 2, No. 1; pp. 99-110; Heteroatom Chemistry.
Fausto Ramirez, et al.; Selectivity of Monomeric Metaphosphate; pp. 1515-1518; Tetrahedron Letters, vol. 23, No. 15, 1982.
F. H. Westheimer; Monomeric Metaphosphates; Aug. 1981; Chemical Reviews, vol. 81, No. 4.
Eli Breuer et al.; Phosphorylation of Alcohols through the Acid–catalysed Fragmentation of α-Oxyimino- (List continued on next page.)

Primary Examiner—Terry J. Owens
Assistant Examiner—Erma Cameron
Attorney, Agent, or Firm—Scully, Scott, Murphy & Presser

[57] ABSTRACT

Solid substrates with free hydroxyl groups are phosphorylated by thermolysing a solution of phosphoramidate of the formula

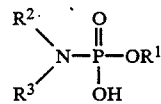

in the presence of the substrate, whereby metaphosphate is generated which phosphorylates the substrate.

14 Claims, No Drawings

OTHER PUBLICATIONS phosphonates; pp. 671–672; J. Chem. Soc., Chem. Commun., 1987.

Malcolm R. Banks et al.; Non–electrophilic Behaviour of Alkyl–substituted Metaphosphates in the Gas Phase: Formation of Alkenes by an Unusual 1,2–Methyl Shift induced by Hydrogen Abstraction—A Methyl Analogue of the Neophyl Ester Rearrangement pp. 1033–1034; J. Chem. Soc., Chem. Commun., 1989.

Weimann et al., "Studies on Polynucleotides. XVII. On the Mechanism of Internucleotide Bond Synthesis by the Carbodiimide Method"; pp. 4329–4341, J. Amer. Chem. Socl (Nov. 1962).

Todd; "Some Aspects of Phosphate Chemistry"; pp. 1389–1397; Proc. N.A.S. (U.S.) vol. 45 (1959).

Todd; "Some Observations on Organic Phosphates", pp. 199–204; Proc. Chem. Soc. (London) (Jun. 1962).

Hamer; Studies in Phosphorylation; Part XXVI; The Mechanism of Phosphorylation by Monoesters of Phosphoramidic Acid; pp. 46–52; J. Chem. Soc. (London), 1965.

V. M. Clark; Studies on Phosphorylation. Part XV. The Use of Phosphoramidic Esters in Acylation. A New Preparation of Adenosine-5' Pyrophosphate and Adenosine-5= Triphosphate; pp. 1497–1501; J. Chem. Soc. (London), 1957.

V. M. Clark et al.; Studies in Phosphorylation. Part XXVIII. The Formation of Pyrophosphates fron Phosphoramidate Monoesters; pp. 5509–5513; J. Chem. Soc. (London), 1965.

PHOSPHORYLATION WITH MONOMERIC METAPHOSPHATES

This invention was made with Government support under Grant No. DAAL-03-89-K-0101 by the Department of Defense (U.S. Army). The Government has certain rights in the invention.

BACKGROUND OF THE INVENTION

The present invention relates to the phosphorylation of substrates to enhance the properties of the substrates and to form new compositions of matter. By "phosphorylation" is meant the creation of O-substituted phosphate ($R^1OPO_3$) groups on the surface of a solid substrate.

Metaphosphoric acid ($HO-PO_2$) and metaphosphates ($RO-PO_2$) are potentially highly useful sources of phosphate groups, since they are extremely reactive, especially to hydroxyl groups. As used herein, "metaphosphate" refers to the monomeric molecule and not to condensed phosphates or polyphosphates, characterized by the presence of $-P-O-P-$ linkages, which are sometimes referred to as metaphosphates. However, that high degree of reactivity also makes the isolation of metaphosphates impossible; the use of metaphosphates as a phosphorylating agent is therefore difficult to carry out. Thus, use of metaphosphate to phosphorylate substrates is difficult and expensive at best, and has not been practiced on a commercial scale.

It has previously been reported that the system 2,3-oxaphosphabicyclo [2.2.2] oct-5-ene-3-oxide undergoes thermal fragmentation in solution to form, for example, ethyl metaphosphate if an ethoxy group is present on the phosphorus (Quin et al., J. Am. Chem. Soc., Vol. 107, pp. 3389-3390 (1985); Quin et al., Tetrahedron Letters, Vol. 31, No. 44, pp. 6281-6282 (1990)). Ethyl metaphosphate formed in this manner has reportedly been used to phosphorylate the surface of silica gel (Quin et al., J. Chem. Soc., Chem. Commun., pp. 555-556 (1988)).

However, adaptation of this procedure to production of meaningful amounts of phosphorylated product on a commercially realistic basis is not practical because of the expense and time required by the complex starting material. It remains desirable to be able to take advantage of the reactivity of metaphosphate. However, a simple, direct method utilizing metaphosphate, in which the starting materials are available, stable, and adaptable to commercially meaningful application, has heretofore not been known.

It has now been determined that the decomposition of the phosphoramidate of formula (1) defined herein and formation of a phosphorylated substrate follows an elimination-addition mechanism, which finding is confirmed by the observation that the reaction follows first-order kinetics. Accordingly, it has now been determined as set forth below that the phosphorylation proceeds via generation of metaphosphate by thermolysis of the phosphoramidate.

SUMMARY OF THE INVENTION

The present invention achieves the desired objectives described herein, while avoiding drawbacks that have heretofore been encountered. It employs readily available starting materials, produces a minimum of by-products that present difficulties in re-use or disposal, and is readily adaptable directly in the phosphorylation of substrates.

Thus, in one aspect, the present invention resides in a process for phosphorylating a solid substrate having surface hydroxyl groups, comprising contacting the surface of said substrate with a solution comprising a compound of the formula

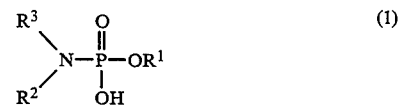

in a solvent which does not undergo nucleophilic attack with metaphosphate of the formula $R^1-OPO_2$, and thermolysing said compound in the presence of said substrate to generate metaphosphate which phosphorylates said substrate, wherein $R^1$ is a straight or branched, saturated or unsaturated alkyl group containing 1 to 60 carbon atoms, wherein the alkyl group optionally contains a linkage of the formula $-O-$, $-S-$, $-NH-$, $-C(O)-$, $-C(O)O-$, $OC(O)-$, $-C(O)NH-$, or $-HNC(O)-$, and is optionally substituted with $-CN$, $-Cl$, $-Br$, $-F$, aryl, aryloxy, heterocyclic, or cyclo-$C_3$-$C_8$-alkyl; or $R^1$ is aryl, heterocyclic, cyclo-$C_3$-$C_8$-alkyl, or bicyclic, tricyclic or polycyclic alkyl, and is optionally substituted with $-CN$, $-Cl$, $-Br$, $-F$, phenyl, benzyl, or straight or branched, saturated or unsaturated alkyl or alkoxy containing up to 12 carbon atoms, the optional phenyl, benzyl, alkyl and alkoxy substituents being optionally substituted with $-CN$, $-Cl$, $-Br$, $-F$, or $C_1$-$C_6$ alkyl;

$R^2$ and $R^3$ are independently hydrogen; or straight or branched, saturated or unsaturated, alkyl containing 1 to 60 carbon atoms and optionally containing a linkage of the formula $-O-$, $-S-$, $-NH-$, $-C(O)-$, $-C(O)O-$, $-OC(O)-$, $-C(O)NH-$ or $-NHC(O)-$, and optionally substituted with $-CN$, $-Cl$, $-Br$, $-F$, aryl, aryloxy, heterocyclic, or cyclo-$C_3$-$C_8$-alkyl; or $R^2$ and $R^3$ are independently selected from the group consisting of bicyclic, tricyclic and polycyclic alkyl, cyclo-$C_3$-$C_8$-alkyl, aryl, and heterocyclic, any of which is optionally substituted with $-CN$, $-Cl$, $-Br$, $-F$, or with phenyl, benzyl, or straight or branched, saturated or unsaturated, alkyl or alkoxy containing up to 12 carbon atoms, the optional phenyl, benzyl, alkyl and alkoxy substituents being optionally substituted with $-CN$, $-Cl$, $-Br$, $-F$, or $C_1$-$C_6$ alkyl;

or $R^2$ and $R^3$ together with the N to which they are attached form a saturated or unsaturated 5 or 6-member ring which optionally contains an oxygen atom or a second nitrogen atom, and which is optionally fused to a phenyl ring.

Another aspect of the present invention is substrates, such as silica gel, zeolites, and cellulosic material, phosphorylated in accordance with the present invention.

DETAILED DESCRIPTION OF THE INVENTION

As indicated, the process of the present invention advantageously starts from phosphoramidate compounds of the formula (1)

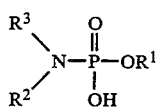 (1)

$R^1$ should be any substituent which will provide the desired properties of the product that is formed when the substrate is phosphorylated. Preferably, $R^1$ is straight or branched alkyl containing 1 to 20 carbon atoms, especially ethyl, and is optionally substituted with halogen, especially chlorine. The halo-substituted groups are especially useful to impart flame retardance when the substrate is cellulosic. $R^1$ can also be alkyl containing 3 to 20 carbon atoms. Substitution with OH and $NH_2$ must be avoided. Other preferred $R^1$ groups include phenyl and benzyl, optionally substituted with one or two alkyl groups containing 1 to 6 carbon atoms; a preferred example of such a group is (+) or (−) menthyl, which when present on the groups used to phosphorylate a chromatographic material usefully imparts the ability to separate optically active isomers.

"Aryl" as used herein is meant to include single-ring aromatic organic systems. Phenyl is the preferred aryl group. "Aryl" as used herein is also intended to cover fused-ring systems in which phenyl is fused to a second ring which is aromatic or partially or wholly unsaturated. Examples of such systems include naphthyl, tetrahydronaphthyl, and indanyl.

"Heterocyclic" as used herein is meant to include single-ring systems which are saturated or unsaturated and which contain a total of 4, 5 or 6 atoms of which 1 or 2 are hetero atoms such as N, O and/or S. Examples of heterocyclic rings include morpholino, pyrazinyl, pyrrolidinyl, pyrrolyl, imidazolinyl, furyl, piperazinyl, isoxazolyl and thienyl. "Heterocyclic" is also meant to encompass systems in which two or more wholly or partially saturated or unsaturated rings are fused together wherein one or more of the rings contains one or two hereto atoms such as N, O or S. Typically, fused two-ring heterocyclic rings systems will contain 8, 9 or 10 atoms. Examples of such fused ring systems include indole, quinoline, isobenzofuran, isoindole, and indoline. Examples of fused three-ring systems include xanthene, carbazole, acridine, phenothiazine and phenoxazine.

"Bicyclic or tricyclic alkyl" as used herein is meant to include adamantyl and norbornyl, regardless of the position at which such a molecule is attached to the phosphoramidate.

$R^2$ and $R^3$ can each be any of a number of substituents, provided only that they do not prevent the desired formation of the metaphosphate nor the subsequent reaction of the metaphosphate with the substrate. In general phosphoramidate, although that thermolysis also proceeds readily when $R^2$ and $R^3$ are both ethyl. Examples of satisfactory $R^2$ groups include straight or branched alkyl containing up to 6 carbon atoms, particularly ethyl; cycloalkyl, especially cyclohexyl; norbornyl (1- or 2-); adamantyl; phenyl; and trimethyl phenyl. Especially preferred are those compounds set forth in Table I. $R^2$ and $R^3$ can also form a ring such as morpholino, piperidinyl, piperazinyl, imidazolinyl, pyrrolidinyl, pyrazinyl, or indolyl.

TABLE 1

| $R^1$ | $R^2$ | $R^3$ |
| --- | --- | --- |
| $C_2H_5$ | 2,4,6-trimethylphenyl | H |
| $C_2H_5$ | $C_2H_5$ | $C_2H_5$ |
| $C_2H_5$ | phenyl | H |
| $C_2H_5$ | 1-adamantyl | H |
| (+)menthyl | phenyl | H |

The compound of formula (1) can be readily prepared from commercially available starting materials. In the preferred synthetic route, a compound of the formula $R^1OP(=O)Cl_2$, either commercially available or formed by the reaction of $POCl_3$ and $R^1OH$, is reacted with $R^2R^3NH$ to displace one of the chlorine atoms with $-NR^2R^3$. The resultant intermediate is then reacted with NaOH to displace the remaining —Cl. Protonation of the derivative thus formed, for instance on a suitable cation exchange resin, forms the desired product of formula (1). Alternatively, reaction with $NaOCH_3$ instead of NaOH can be followed by reaction with trimethylamine and then protonation on the cation exchange resin.

Compounds of formula (1) are preferably formed at or below room temperature in solution in an aprotic solvent. Preferred solvents include toluene, acetonitrile, dimethyl formamide, DMSO, and chlorobenzene. Solvents with nucleophilic groups, such as water and alkanols, should be avoided. The compound of formula (1) can be recovered from solution, and then redissolved to carry out the phosphorylation, but the solution in which the compound of formula (1) is formed can also be used directly for the phosphorylation. In the latter case it is preferable to prepare the compound of formula (1) shortly before the phosphorylation is to be carried out, in order to minimize unwanted decomposition of the compound of formula (1).

The phosphorylation is carried out in solution in a solvent meeting the conditions described hereinabove. All materials, reagents and equipment used must be free of water and protic solvents. The reaction is carried out by contacting a solution of a compound of formula (1), with the substrate and then heating the solution to a temperature at which the decomposition of the phosphoramidate(1) begins, and maintaining it at a temperature at which the reaction continues to completion. Preferably, the solution is agitated to improve contact with the substrate. Satisfactory temperatures are on the order of about 50° C. to about 125° C., although higher or lower temperatures may be employed if conditions warrant provided that the phosphorylation proceeds and side reactions are minimized. Suitable steps should be taken to assure that the solvent does not evaporate away from the reaction mixture during the reaction. Thus, the reaction is preferably carried out under reflux.

Contact of the solution of the compound of formula (1) with the substrate to be phosphorylated should last for a period of time sufficient to effect completion of the thermal decomposition of the phosphoramidate (1). That period of time is a function of the concentration of the phosphorylating reagent. The appropriate reaction time can readily be determined for any particular set of conditions by e.g. monitoring the phosphoramidate concentration of the solution; when the phosphoramidate concentration reaches zero the phosphorylation reaction is complete. Any concentration of the phosphorylating reagent can be used; effective phosphorylation is provided with a concentration of the compound of formula (1) of generally about 0.05M to about 0.3M, although higher concentrations are more efficient and useful. Following phosphorylation, the substrate is recovered from the solution and dried.

Suitable substrates can comprise any material having pendant hydroxyl groups at the surface. Particularly preferred substrates include cellulosic material, by which is meant cellulose, cellulosic derivatives which have been partially converted to e.g., cellulose acetate, cellulose acetate butyrate, and the like, such that some of the —OH groups remain on the cellulose backbone, and hydroxy —$C_{1-12}$ alkyl derivatives such as hydroxylpropyl cellulose and hydroxyethyl cellulose which are bonded to the cellulose backbone and have free —OH groups; silica gel; zeolites; and inorganic oxides and mixed oxides such as silicates, aluminates, aluminosilicates, alumina, and titanium dioxide provided they have some surface hydroxyl groups.

Cellulose phosphorylated in accordance with the present invention provides material useful as chromatographic packing. Phosphorylation in accordance with the present invention of cellulosic surfaces (by which is meant material containing cellulose and/or cellulosic material (defined above) in woven or unwoven form, such as fabric and paper, provided that there are free —OH groups available to be phosphorylated) is useful in that it provides reduction in the flammability of fabrics, paper and other materials made in whole or in part of cellulosic material. The effectiveness of the present invention in imparting flame retardancy to a cellulosic paper surface has been demonstrated.

Phosphorylation of silica gel in accordance with the present invention is useful in that it provides a product useful in chromatographic applications such as HPLC. Such products can consist entirely of silica gel, or can comprise a surface layer of silica gel on a base of another material. Phosphorylation with compounds wherein $R^1$ is asymmetric, or optically active, such as sec-butyl or menthyl (either essentially entirely in the (+) form, or essentially entirely in the (−) form), is especially useful as it provides chromatographic material that provides separation of chiral isomers.

Phosphorylation of zeolites (crystalline aluminosilicates useful as catalysts and molecular sieves) would usefully affect the selectivity, cavity size, and affinities of the zeolites. Phosphorylation of the zeolite with an optically active $R^1$ group (e.g. (+) menthyl or (−) menthyl) would also usefully mediate the ability to carry out asymmetric syntheses.

The invention will be described further in the following Examples, which are provided for purposes of illustration and not for limitation.

In the Examples, $^{31}P$ NMR solution spectra (FT, $^1H$-decoupled) were recorded on an IBM-NR 80 spectrometer at 32.38 MHz; 85% $H_3PO_4$ was used as the standard, with an external deuterium lock. Downfield shifts are positive. $^{31}P$ solid NMR spectra were recorded on a Bruker 200 MHz spectrometer; $CaHPO_4$ was used as the reference, using the CP-MAS technique.

EXAMPLE 1

A. Synthesis of Salt of Phosphoramidate

Ethyl dichlorophosphate (Aldrich; 30 mmol) was reacted with 30 mmol of 2,4,6-trimethylaniline in carbon tetrachloride solution in the presence of 30 mmol of triethylamine. Triethylamine hydrochloride was filtered, solvent was evaporated, and the residue of (EtO)(MesNH)POCl ($^{31}P$ $\delta10.2$) was then hydrolyzed with NaOH in acetone-water solution. The resulting salt $Na^+EtOP(O)(MesNH)O^-$ was dried in vacuo over $P_2O_5$ to give a light-brown viscous residue (yield 80%, $^{31}P$ $\delta4.9$).

B. Conversion of Salt into Acid

The salt (1 mmol) was suspended or dissolved in 5 mL of toluene, then 5 mL of ethanol, and then 2 g of AMBERLYST ion exchange resin (Fluka) were added. The suspension was stirred for 3 min., and then the resin was separated and washed with dry toluene. The combined toluene filtrates were immediately evaporated to dryness on a rotary evaporator, and then further dried at 0.1–1.0 mm Hg. This gave the acid ($^{31}P$ $\delta6.2$) as a semicrystalline solid, yield 70–80%.

EXAMPLE 2

A. Synthesis of Salt

The tetramethylammonium salt of O-ethyl-N,N-diethylaminophosphoric acid was synthesized by modification of a known method (J. Cheynol et al., Compt. Rend., Vol. 251, 550 (1960)). $EtOP(O)Cl_2$ (30 mmol) was reacted with two molar equivalents of $HNEt_2$ in carbon tetrachloride solution. Diethylamine hydrochloride was filtered off and the solvent was removed. The residue of $EtOP(O)ClNEt_2$ ($^{31}P$ $\delta14.3$) was further converted by treatment with solid MeONa suspended in ether. The crude $EtOP(O)OMe(NEt_2)$ ($^{31}P$ $\delta10.8$) was placed in acetone solution for reaction with an excess of trimethylamine in a sealed ampoule at 100° C. The resulting tetramethylammonium salt was twice crystallized from acetone; mp 246.5°–247.8° C., yield 14%, $^{31}P$ $\delta7.4$.

B. Conversion of Salt to Acid

The salt was converted to the acid following the procedure set forth in part B. of Example 1. This gave the acid ($^{31}P$ $\delta11.2$) as a semicrystalline solid, yield 70–80%.

EXAMPLE 3

Phosphorylation of Silica Gel

1 Mmol of freshly-prepared $EtOP(O)OH(NEt_2)$ prepared in accordance with Example 2 was placed in 10 mL of dry toluene and the solution was transferred into an ampoule with 1 g of dry silica gel (Aldrich, 70–230 mesh, 60Å, B.E.T. surface area ca. 500 $m^2g^{-1}$, pore volume 0.75 $cm^3g^{-1}$). The silica gel has been dehydrated at 195° C. for 96 hrs at 0.1 Torr. The ampoule was sealed under argon (nitrogen and other gases inert to these materials could also be used). The suspension was heated to 100° C. for 80 min. The solid product was recovered by filtration and washed three times with cold isopropanol. (CP-MAS $^{31}P$ NMR signal at $\delta-10.0$. This signal indicates covalently bound phosphorus). The same value is found when $EtOPO_2$ has been generated from thermolysis of a substituted 2,3-oxaphosphabicyclo[2.2.2] octene or from acid-promoted fragmentation of ethyl α-(oxyimino) benzyl phosphonate.

EXAMPLE 4

Synthesis of O-ethyl-N-phenyl amidochlorophosphate

A solution of 2.33 g (25 mmol) of aniline and 2.52 g (25 mmol) of triethylamine in 30 ml of dry ethyl ether was slowly dropped into a solution of 4.08 g (25 mmol) of ethyl dichlorophosphate in 30 ml of ether. After 30 min the insoluble triethylamine hydrochloride was filtered and the solvent was evaporated (yield 62%, $^{31}$P NMR δ 8.9 (CDCl$_3$))

Synthesis of O-Ethyl-N-Phenyl Amidophosphoric Acid Sodium Salt

A solution of 0.240 g (6 mmol) of NaOH in 5 ml of water was dropped into a solution of O-ethyl-N-phenyl amidochlorophosphate (0.440 g., 2 mmol) in 5 ml of acetone and the solution was stirred for an hour. The solvent was evaporated and the residue was dried in vacuo. The phosphorus compound was dissolved in absolute ethanol and separated from insoluble NaCl by centrifugation. Evaporation of alcohol gave a white solid, $^{31}$P NMR δ 0.98 (CDCl$_3$), yield 70%.

Conversion of Sodium Salt into O-Ethyl-N-Phenyl Amidophosphoric Acid

O-ethyl-N-phenyl amidophosphoric acid sodium salt (0.200 g, 0.89 mmol) was dissolved in 10 ml of methanol and passed through an AMBERLYST (2 g) column. The acid was washed with 40 ml of methanol. The solvent was evaporated, and the residue was washed with dry toluene. Evaporation of solvent gave the acid (yield 80%, $^{31}$P NMR δ 2.77 (CDCl$_3$)) as a viscous residue.

Phosphorylation of silica gel with O-ethyl-N-phenyl amidophosphoric acid

A suspension of 0.995 g of silica gel (Exmere EXSIL 100 HPLC grade, 5 μm, 100 Angstrom pore diameter, 200 m$^2$/g surface area, 0.5 cm$^3$/g pore volume) and 0.1619 g (0.8 mmol) of O-ethyl-N-phenyl amidophosphoric acid in 10 ml of dry toluene was heated at 90° C. for 40 min. The solid product was recovered by filtration, washed twice with isopropanol and dried. CP/MAS $^{31}$P NMR δ-9.89, $^{29}$Si δ-113 (this signal, which is the signal for Si with bound phosphate groups, occurs at the same point as the signal for Si bearing no —OH groups. The signal for Si bearing one —OH group, δ-103, was greatly diminished at the end of this step.)

EXAMPLE 5

Synthesis of O-Ethyl-N-1-Adamantyl Amidochlorophosphate

A solution of 3.90 g (25 mmmol) of 1-adamantylamine and 2.52 g (25 mmol) of triethylamine in 30 ml of dry ethyl ether was added to a solution of 4.08 g (25 mmol) of ethyl dichlorophosphate in 30 ml of ether. After 20 hours at room temperature the insoluble triethylamine hydrochloride was filtered and the solvent was evaporated. The crude product was crystallized from chloroform-hexane solution which gave white needles (m.p. 125.4°–126.8° C.) (yield 67%, $^{31}$P NMR δ 10.5 (CDCl$_3$)).

Synthesis of O-ethyl-N-1-adamantyl amidophosphoric acid sodium salt

O-Ethyl-N-1-adamantyl amidochlorophosphate (6.95 g, 25 mmol) was dissolved in 60 ml of acetone-water solution containing NaOH (2 g, 50 mmol); after 5 min. the reaction was completed. The solvents were evaporated and solid was dried in vacuo. The salt of amidophosphoric acid was dissolved in absolute ethanol and NaCl was filtered. The ethanol solution after evaporation gave white solid, (yield 85%, $^{31}$P NMR δ 5.04 (water-acetone).

Conversion of sodium salt into O-ethyl-N-1-adamantyl amidophosphoric acid

The sodium salt of O-ethyl-N-1-adamantyl amidophosphoric acid (0.513 g, 1.82 mmol) was dissolved in methanol (10 ml) and passed through Amberlyst (7 g), and the resulting O-ethyl-N-1-adamantyl amidophosphoric acid was washed with 50 ml of methanol. The methanol was evaporated, and the residual white solid was dissolved in 200 ml of chloroform, filtered and concentrated to about 30 ml. The product crystallized as white fine needles (m.p. 126.4°–127° C.), yield 95%, $^{31}$P NMR δ 9.29 (CDCl$_3$).

Phosphorylation of Silica Gel with O-Ethyl-N-1-Adamantyl Amidophosphoric Acid A suspension of 0.696 g of silica gel and 0.1743 g (0.67 mmol) of O-ethyl-N-1-adamantyl amidophosphoric acid in 10 ml of dry toluene was heated at 110° C. for 90 min. The reaction product was recovered by filtration, washed two times with isopropanol and dried. (CP/MAS $^{31}$P NMR δ-10.3, $^{29}$Si δ-113). The absence of a signal at $^{29}$Si δ-103 indicated the absence of Si-OH groups.

EXAMPLE 6

Synthesis of O-(+)-menthyl dichlorophosphate

A solution of 7.5 g (48 mmol) of (1S, 2R, 5S)-(+)-menthol (Aldrich) and 4.86 g (48 mmol) of triethylamine in 20 ml of toluene was dropped into 7.36 g (48 mmol) of POCl$_3$ at 0° C. The entire solution was stirred for 23 hours at room temperature. The insoluble triethylamine hydrochloride was filtered and the solvent was evaporated. Yield 99%, $^{31}$P NMR δ 6.76 (CDCl$_3$). (lit. T. Milobedzki, W. Janczak, Roczniki Chemji 11, 840 (1931)).

Synthesis of O-(+)-menthyl N-phenyl-chlorophosphate

A solution of 4.42 g (47.5 mmol) of aniline and 4.81 g (47.5 mmol) of triethylamine in 60 ml of dry ethyl ether was dropped at 0° C. into a solution of 12.97 g (47.5 mmol) of O-(+)menthyl dichlorophosphate in 60 ml of ether. The entire solution was stirred for 20 hours at room temperature. The insoluble triethylamine hydrochloride was filtered; the solvent was evaporated and the residue was dried in vacuo. Yield 93%, $^{31}$P NMR δ 6.61 and 7.06 (CDCl$_3$).

Synthesis of O-(+)Menthyl N-Phenyl-Phosphoramidic Acid Sodium Salt

A solution of 10.6 g (266 mmol) of NaOH in 110 ml of water was dropped into a solution of 14.6 g (44.3 mmol) of O-(+)menthyl N-phenyl-chlorophosphate in 110 ml of acetone. The entire solution was stirred for 1 hour. The solvent was evaporated and the residue was dried in vacuo. The resulting phosphorus compound was dissolved in chloroform/methanol (10:1) and separated by filtration from the insoluble NaCl and NaOH. The solvent was evaporated and residue was dried in vacuo. Yield 57%, $^{31}$P NMR δ 0.65 (CDCl$_3$).

Synthesis of O-(+)menthyl N-phenyl-phosphoramidic acid

Sodium salt of O-(+)menthyl-N-phenyl-phosphoramidic acid (0.2367 g, 0.71 mmol) was dissolved in 10 ml of methanol and passed through 2 g of AMBERLYST; the resin column was washed with 40 ml of methanol. The solvent was evaporated quickly and the residue was dried in vacuo and then dissolved in dry toluene and filtered. The solvent was evaporated and the residue was dried in vacuo. Yield 94%, $^{31}$P NMR $\delta$ 3.05(CDCl$_3$).

Phosphorylation of silica gel with O-(+)menthyl N-phenyl-phosphoramidic acid

A solution of O-(+)menthyl N-phenyl-phosphoramidic acid (0.963 g, 3.1 mmol) in 70 ml of toluene was transferred to 6.5 g of EXSIL 100 HPLC grade silica, and the suspension was stirred for 150 min at 105° C. The reaction product was recovered by filtration and washed twice with isopropanol. CP/MAS $^{31}$P NMR $\delta$-6.5.

EXAMPLE 7

Phosphorylation of Cellulose

To a solution of EtOP(O)OH(NHPh) (0.5 mmol) in 5 ml of dry toluene was added 1.0 g of dry cellulose (Aldrich Chemical Col, 20 micron). The suspension was stirred and refluxed for 15 min. The solid was recovered by filtration and washed four times with isopropyl alcohol. The dried solid had $^{31}$P NMR $\delta$1.9 and $-8.9$, in nearly equal peak size. The signal at $\delta$1.9 is attributed to an ethyl phosphate group bonded to one (or more) of the cellulose hydroxy sites. The signal at $-8.9$ was greatly diminished by washing the solid with water; this behavior, as well as its $^{31}$P NMR shift, suggest that a pyrophosphate group has also been bonded to the solid.

EXAMPLE 8

HPLC grade silica gel (EXSIL 100) which had been phosphorylated with CH$_3$CH$_2$OPO$_3$ groups in accordance with the present invention was used in a HPLC column to which was applied a mixture containing amounts of each of the components shown in the following Table. The components were indeed separated, as can be seen from the range of capacity factors for the various components:

| Component | Capacity Factor | |
|---|---|---|
| | 3 cm column* | 25 cm column** |
| Hexane | 0.1 | 0.1 |
| Hexadecane | 0.1 | 0.1 |
| Naphthalene | 0.6 | 1.8 |
| Phenanthrene | 0.8 | 2.9 |
| Anthracene | 0.8 | 2.1 |
| Dibenzothiophene | 0.4 | 1.8 |
| Thianthrene | 0.4 | 2.0 |
| 9-Nitroanthracene | 1.0 | 5.8 |
| 1-Nitronaphthalene | 2.5 | 5.1 |
| 1-Cyanonaphthalene | 2.4 | 8.6 |
| 4-Isopropylphenol | 9.6 | 11.7 |
| p-Dodecylphenol | 4.8 | 10.2 |
| 2,4-Dimethylphenol | 5.0 | 9.2 |
| 9-Fluorenone | 3.6 | 10.3 |
| Anthraquinone | 10.4 | 9.6 |
| 2-Methylindole | 2.5 | 7.7 |
| Carbazole | 2.2 | 5.1 |
| 1-Naphthol | 5.6 | 11.8 |
| 2-Naphthol | 9.7 | 12.7 |
| 3-Aminofluoranthene | 19.8 | 17.8 |
| 2-Aminoanthracene | 23.2 | 14.6 |
| Quinoline | 22.0 | 15.7 |
| Quinaldine | 19.6 | 14.4 |
| 7,8-Benzoquinoline | 20.2 | 19.6 |

*100% cyclohexane for 15 min., ramp to 90% cyclohexane-10% 2-PrOH in 15 min., 2 ml/min.
**100% cyclohexane for 10 min., 1 ml./min., ramp to 40% cyclohexane-60% methylenechloride during 10 min. to 30 min. at 2 ml/min.

EXAMPLE 9

Chromatograms of 2,4-dimethylaniline were taken on a column containing untreated EXSIL 100 HPLC-grade silica gel and on a column containing EXSIL 100 HPLC-grade silica gel that had been phosphorylated with CH$_3$CH$_2$OPO$_3$ in accordance with the present invention. The run using the untreated silica gel (10 $\mu$l injection volume; 250×4.6 mm column; mobile phase, 97% cyclohexane/3% 2-propanol; flow rate, 1 ml/min; detection: UV @ 254 nm) gave a broad, low peak with a large tail. The run using the treated silica gel (10 $\mu$l injection volume; 250×4.6 mm column; mobile phase, 90% cyclohexane/10% 2-propanol; flow rate, 0.75 ml/min; detection: UV @ 254 nm) gave a high, sharp peak with only a minor tail. The latter is, of course, a highly preferable result.

EXAMPLE 10

Two chromatograms were run to demonstrate the separation achievable with HPLC grade silica gel that had been phosphorylated with CH$_3$CH$_2$OPO$_3$ in accordance with the present invention.

In one run, 2,4,6-trimethylaniline, 1-aminonaphthalene, and 2-aminoanthracene successfully eluted separately on a 250×4.5 mm column of phosphorylated Exsil 100 silica gel (mobile phase: 97% cyclohexane/3% 2-propanol; flow rate, 1 ml/min; detection, UV @ 254 nm).

In another run, acetophenone, benzophenone, and acetone successfully eluted separately on a 250×4.6 mm column of phosphorylated EXSIL 100 silica gel (mobile phase: 100% cyclohexane 10 min., then up to 4% 2-propanol in 20 min.; flow rate, 0.75 ml/min.; detection, UV @ 280 nm).

EXAMPLE 11

Exsil 100 HPLC grade silica gel was phosphorylated with O-(+)menthyl-N-phenylphosphoramidic acid in accordance with the present invention to produce an optically active substituent on the silica gel. The performance of this product as a chromatographic packing (250×4.6 mm) was evaluated using a racemic mixture of [R,S]-2-phenylcyclohexanone dissolved in isopropanol (0.15 mg/mL). At a flow rate of 0.5 mL/min. using methylene chloride as the mobile phase, the [R] and [S] isomers were eluted as separate peaks.

The experiment was repeated to attempt to resolve a solution of [R,S]-benzoin. At a flow rate of 1 mL/min in methylene chloride, a sufficient difference in retention time was observed to separate the two isomers.

EXAMPLE 12

A sample of Zeolite Y (1 g, dried at 350° C. for 2 hrs) was suspended in a solution of 0.1 g of N-adamantyl-O-ethyl phosphoramidate in 10 ml of dry toluene. This suspension was sealed in a glass tube at 130° C. for 1.75 hrs. The product was then found to exhibit a major peak at $^{31}$P $\delta$-13.0 and a minor peak at $^{31}$P $\delta$-0.1. At the beginning of the procedure, there were $^{29}$Si peaks of equal intensity at δ-101 and δ-105.9. After the procedure, the $^{29}$Si δ-105.9 remained, and the other peak has shifted to δ-111 but retained equal intensity.

What is claimed is:

1. A process for phosphorylating a solid substrate having surface hydroxyl groups, comprising contacting the surface of said substrate with a solution comprising a compound of the formula (1)

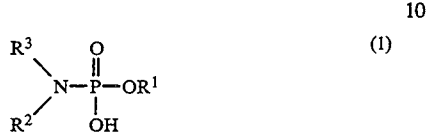

in a solvent that does not undergo nucleophilic attack with metaphosphate of the formula $R^1$-$OPO_2$, and then heating the solution to thermolyse said compound in the presence of said surface to generate metaphosphate in solution whereby said metaphosphate phosphorylates said substrate, wherein $R^1$ is a straight or branched, saturated or unsaturated alkyl group containing 1 to 60 carbon atoms, wherein the alkyl group optionally contains a linkage of the formula —O—, —S—, —NH—, —C(O)—, —C(O)O—, OC(O)—, —C(O)NH—, or —HNC(O)—, and is optionally substituted with —CN, —Cl, —Br, —F, aryl, aryloxy, heterocyclic or cyclo-$C_3$-$C_8$-alkyl; or $R^1$ is aryl, heterocyclic, cyclo-$C_3$-$C_8$-alkyl, or bicyclic, tricyclic or polycyclic alkyl, and is optionally substituted with —CN, —Cl, —Br, —F, phenyl, benzyl, or straight or branched, saturated or unsaturated alkyl or alkoxy containing up to 12 carbon atoms, the optional phenyl, benzyl, alkyl and alkoxy being optionally substituted with —CN, —Cl, —Br, —F, or $C_1$-$C_6$ alkyl;

$R^2$ and $R^3$ are independently hydrogen; or straight or branched, saturated or unsaturated, alkyl containing 1 to 60 carbon atoms and optionally containing a linkage of the formula —O—, —S—, —NH—, —C(O)—, —C(O)O—, —OC(O)—, —C(O)NH— or —NHC(O)—, and optionally substituted with —CN, —Cl, —Br, —F, aryl, aryloxy, heterocyclic, or cyclo-$C_3$-$C_8$-alkyl; or $R^2$ and $R^3$ are independently selected from the group consisting of bicyclic, tricyclic and polycyclic alkyl, cyclo-$C_3$-$C_8$- alkyl, aryl, and heterocyclic, any of which is optionally substituted with —CN, —Cl, —Br, —F, or with phenyl, benzyl, or straight or branched, saturated or unsaturated, alkyl or alkoxy containing up to 12 carbon atoms, the optional phenyl, benzyl, alkyl and alkoxy substituents being optionally substituted with —CN, —Cl, —Br, —F, or $C_1$-$C_6$ alkyl;

or $R^2$ and $R^3$ together with the N to which they are attached form a saturated or unsaturated 5 or 6-member ring which optionally contains an oxygen atom or a second nitrogen atom, and which is optionally fused to a phenyl ring.

2. The process of claim 1 wherein $R^1$ is alkyl or alkoxy containing 1 to 20 carbon atoms, which is optionally substituted with —Cl, —Br, or —F, or $R^1$ is phenyl or phenoxy which is optionally substituted with —Cl, —Br, —F, or alkyl containing up to 12 carbon atoms.

3. The process of claim 1 wherein $R^3$ is hydrogen or alkyl containing up to 20 carbon atoms which is optionally substituted with —CN, —Cl, —Br, —F or phenyl.

4. The process of claim 1 wherein $R^2$ and $R^3$ are ethyl.

5. The process of claim 1 wherein $R^1$ is optically active.

6. The process of claim 1 wherein $R^3$ is hydrogen.

7. The process of claim 6 wherein $R^2$ is 1-adamantyl or 2-adamantyl and is optionally substituted with —CN, —Cl, —Br, —F or alkyl containing up to 6 carbon atoms.

8. The process of claim 6 wherein $R^2$ is phenyl and is optionally substituted with —CN, —Cl, —Br, —F or alkyl containing up to 6 carbon atoms.

9. The process of claim 1 wherein said substrate comprises cellulose.

10. The process of claim 1 wherein said substrate is cellulosic fiber or cellulosic fabric.

11. The process of claim 1 wherein said substrate comprises silica gel.

12. The process of claim 11 wherein $R^1$ is optically active.

13. The process of claim 12 wherein $R^1$ is menthyl that is essentially entirely in the (+) form or essentially entirely in the (−) form.

14. The process of claim 1 wherein the substrate is a zeolite.

* * * * *